United States Patent
Connolly et al.

(10) Patent No.: US 7,598,399 B2
(45) Date of Patent: Oct. 6, 2009

(54) METHODS FOR SYNTHESIS OF 3-AMINO-1-ARYLPROPYL INDOLES

(75) Inventors: Terrence Joseph Connolly, Warwick, NY (US); Robert P. Farrell, Mountain View, CA (US); Eric Roy Humphreys, San Bruno, CA (US); Stephen M. Lynch, San Jose, CA (US); Keshab Sarma, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 499 days.

(21) Appl. No.: 11/605,648

(22) Filed: Nov. 29, 2006

(65) Prior Publication Data

US 2007/0135647 A1 Jun. 14, 2007

Related U.S. Application Data

(60) Provisional application No. 60/741,516, filed on Nov. 30, 2005.

(51) Int. Cl.
C07D 209/18 (2006.01)
(52) U.S. Cl. ...................................... 548/495
(58) Field of Classification Search ............ None
See application file for complete search history.

(56) References Cited

U.S. PATENT DOCUMENTS

| | | | |
|---|---|---|---|
| 2,708,197 A | 5/1955 | Speeter | |
| 2,752,358 A | 6/1956 | Ehrhart et al. | |
| 2,984,670 A | 5/1961 | Szmuszkovicz et al. | |
| 2005/0222148 A1 | 10/2005 | Kim et al. | |

FOREIGN PATENT DOCUMENTS

| | | |
|---|---|---|
| CN | 1 513 847 A | 7/2004 |
| DE | 849 108 | 9/1952 |
| EP | 0 600 830 A1 | 11/1993 |
| EP | 0 775 694 A2 | 5/1997 |
| EP | 0 775 694 A3 | 5/1997 |
| EP | 0 887 348 A1 | 12/1998 |
| FR | 2 814 073 A1 | 3/2002 |
| GB | 705652 | 3/1954 |
| GB | 992731 | 5/1965 |
| JP | 3-14562 A2 | 1/1991 |
| WO | WO 94/12478 A1 | 6/1994 |
| WO | WO 96/40097 A1 | 12/1996 |
| WO | WO 97/10219 A1 | 3/1997 |
| WO | WO 97/46511 A1 | 12/1997 |
| WO | WO 98/43942 A1 | 10/1998 |
| WO | WO 99/16755 A1 | 4/1999 |
| WO | WO 99/21553 A1 | 5/1999 |
| WO | WO 99/21557 A1 | 5/1999 |
| WO | WO 00/02551 A2 | 1/2000 |
| WO | WO 01/32622 A1 | 5/2001 |
| WO | WO 02/069965 A1 | 9/2002 |
| WO | WO 2005/118539 A1 | 12/2005 |

OTHER PUBLICATIONS

Ganellin, C.R., et al., "Aminoalkylation of Metal Derivatives of Indole: Part III." *J. Chem Society*, Section C (Organic), vol. 11, 1969, pp. 1537-1540.
Kononova, V. V., et. al. "Carbolines IX Synthesis of 1-methyl-2-chloro-4-aryl-alpha-isocarbolines," *Izvestiya Sibiraskogo otdeleniya Akademii Nauk SSSR, Seriya Khimicheskikh Nauk*, vol. 3 (1979) pp. 147-150.
Lindner, E. "Über ein neues Antihistaminicum, das—1-Pyridyl-(2)-3-dimenthylaminopropan und sein Salz mit der p-Aminosalicylsäure (A vil)," *Naunyn-Schmiedbergs Archiv für Pharmakologie und Experimentelle Pathologie*, vol. 211 (1950) pp. 328-344.
Stanetty, P. et. al. "Synthese neuer Indolmethanamine durch Leimgruber-Batcho Reakton," *Arch. Pharm.*, vol. 325 (1992) pp. 433-437.
Zhou, J. et. al., "Controllable Enantioselective Friedel-Crafts Reaction[1] between Indoles and Alkylidene Malonates Catalyzed by Pseudo-$C^3$-Symmetric Trisoxazoline Copper (II) Complexes," *J. Org. Chem.*, vol. 69 (2004) pp. 1309-1320.
Zhou, J. et. al., "Sidearm Effect: Improvement of the Enantiomeric Excess in the Asymmetric Michael Addition[‡] of Indoles to Alkylidene Malonates," *J. Am. Chem. Soc.*, vol. 124 (2002) pp. 9030-9031.

*Primary Examiner*—Kamal A Saeed
(74) *Attorney, Agent, or Firm*—Robert C. Hall

(57) ABSTRACT

A method comprising:
hydrogenating an indole propionamide compound of formula h

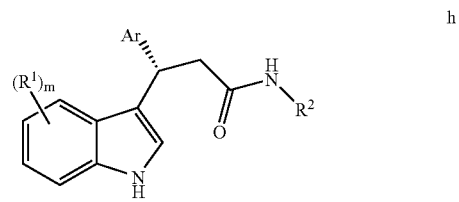

with vitride, to form an aminopropyl indole compound of formula i

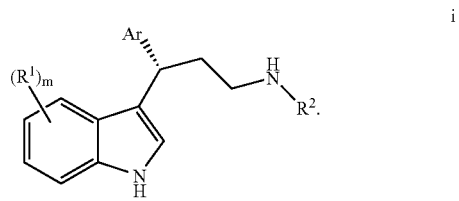

wherein m, Ar, $R^1$ and $R^2$ are as defined herein. The compounds prepared by the method of the invention are useful as monoamine reuptake inhibitors useful for treatment of CNS indications.

15 Claims, No Drawings

METHODS FOR SYNTHESIS OF 3-AMINO-1-ARYLPROPYL INDOLES

CROSS REFERENCE TO RELATED APPLICATIONS

This application is entitled to the benefit of provisional patent application Ser. No. 60/741,516 filed on Nov. 30, 2005, the disclosure of which is incorporated herein by reference.

FIELD OF THE INVENTION

This invention pertains to 3-amino-1-arylpropyl substituted heteroaryl compounds usable as monoamine reuptake inhibitors. In particular, processes and intermediates are disclosed for making such compounds.

BACKGROUND OF THE INVENTION

Monoamine deficiency has been long been linked to depressive, anxiolytic and other disorders (see, e.g.: Charney et al., *J. Clin. Psychiatry* (1998) 59, 1-14; Delgado et al., *J. Clin. Psychiatry* (2000) 67, 7-11; Resser et al., *Depress. Anxiety* (2000) 12 (Suppl 1) 2-19; and Hirschfeld et al., *J. Clin. Psychiatry* (2000) 61, 4-6. In particular, serotonin (5-hydroxytryptamine) and norepinephrine are recognized as key modulatory neurotransmitters that play an important role in mood regulation. Selective serotonin reuptake inhibitors (SSRIs) such as fluoxetine, sertraline, paroxetine, fluvoxamine, citalopram and escitalopram have provided treatments for depressive disorders (Masand et al., *Harv. Rev. Psychiatry* (1999) 7, 69-84). Noradrenaline or norepinephrin reuptake inhibitors such as reboxetine, atomoxetine, desipramine and nortryptyline have provided effective treatments for depressive, attention deficit and hyperactivity disorders (Scates et al., *Ann. Pharmacother.* (2000) 34, 1302-1312; Tatsumi et al., *Eur. J. Pharmacol.* (1997) 340, 249-258).

Enhancement of serotonin and norepinephrine neurotransmission is recognized to be synergistic in the pharmacotherapy of depressive and anxiolytic disorders, in comparison with enhancement of only serotonin or norepinephrine neurotransmission alone (Thase et al., *Br. J. Psychiatry* (2001) 178, 234, 241; Tran et al., *J. Clin. Psychopharmacology* (2003) 23, 78-86). Dual reuptake inhibitors of both serotonin and norepinephrine, such as duloxetine, milnacipran and venlafaxine are currently under development for treatment of depressive and anxiolytic disorders (Mallinckrodt et al., *J. Clin. Psychiatry* (2003) 5(1) 19-28; Bymaster et al., *Expert Opin. Investig. Drugs* (2003) 12(4) 531-543). Dual reuptake inhibitors of serotonin and norepinephrine also offer potential treatments for schizophrenia and other psychoses, dyskinesias, drug addition, cognitive disorders, Alzheimer's disease, obsessive-compulsive behaviour, attention deficit disorders, panic attacks, social phobias, eating disorders such as obesity, anorexia, bulimia and "binge-eating", stress, hyperglycaemia, hyperlipidemia, non-insulin-dependent diabetes, seizure disorders such as epilepsy, and treatment of conditions associated with neurological damage resulting from stroke, brain trauma, cerebral ischaemia, head injury and haemorrhage. Dual reuptake inhibitors of serotonin and norepinephrine also offer potential treatments for disorders and disease states of the urinary tract, and for pain and inflammation.

There is accordingly a need for compounds that are effective as serotonin reuptake inhibitors, norepinephrine reuptake inhibitors, and/or dual reuptake inhibitors of serotonin and norepinephrine, as well as methods of making and using such compounds in the treatment of depressive, anxiolytic, genitourinary, and other disorders. There is a corresponding need for methods of making such compounds.

SUMMARY OF THE INVENTION

The invention provides a method comprising:
hydrogenating an indole propionamide compound of formula h

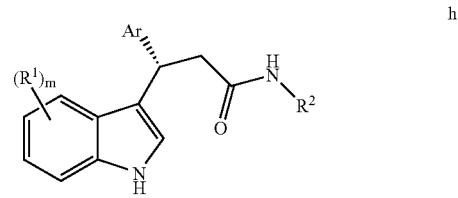

wherein:
m is from 0 to 4;
Ar is optionally substituted aryl or optionally substituted heteroaryl;
each $R^1$ is independently alkoxy, cyano, alkyl, halo, $-S(O)_rR^a$; or $-C(=O)NR^bR^c$ wherein r is an integer from 0 to 2, and each of $R^a$, $R^b$, and $R^c$ is independently hydrogen or alkyl; and
$R^2$ is alkyl;

with vitride, to form an aminopropyl indole compound of formula i

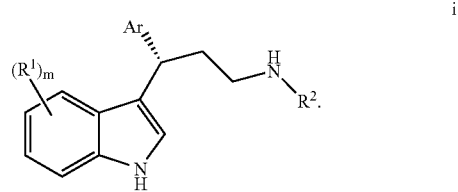

wherein m, Ar, $R^1$ and $R^2$ are as defined herein.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, "Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, tert-butoxy and the like.

"Alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —SO$_2$— and R" is alkyl as defined herein.

"Alkylsulfonylalkyl" means a moiety of the formula $R^a$—SO$_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkylsulfonyloxy" means a moiety of the formula $R^a$—SO$_2$—O—, where $R^a$ is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aryloxy" means a moiety of the formula —OR, wherein R is an aryl moiety as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkyloxy" and "cycloalkoxy", which may be used interchangeably, mean a group of the formula —OR wherein R is cycloalkyl as defined herein. Exemplary cycloalkyloxy include cyclopropyloxy, cyclobutyloxy, cyclopentyloxy, cyclohexyloxy and the like.

"Cycloalkylalkyl" means a moiety of the formula —R'—R", where R' is alkylene and R" is cycloalkyl as defined herein.

"Cycloalkylalkyloxy" and "cycloalkylalkoxy", which may be used interchangeably, mean a group of the formula —OR wherein R is cycloalkylalkyl as defined herein. Exemplary cycloalkyloxy include cyclopropylmethoxy, cyclobutylmethoxy, cyclopentylmethoxy, cyclohexylmethoxy and the like.

"Heteroalkyl" means an alkyl radical as defined herein, including a branched $C_4$-$C_7$-alkyl, wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" and "heteroaralkyl", which may be used interchangeably, mean a radical-$R^aR^b$ where $R^a$ is an alkylene group and $R^b$ is a heteroaryl group as defined herein The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. Examples of haloalkoxy moieties include, but are not limited to, trifluoromethoxy, difluoromethoxy, 2,2,2-trifluoroethoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", phenyl", "heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzofuranyl such as benzofuran-2-yl and benzofuran-3-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl)" or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, acylamino, mono-alkylamino, di-alkylamino, hydroxyalkyl, alkoxyalkyl, benzyloxy, cycloalkylalkyl, cycloalkoxy, cycloalkylalkoxy, alkylsulfonyloxy, optionally substituted thienyl, optionally substituted pyrazolyl, optionally substituted pyridinyl, morpholinocarbonyl, —(CH$_2$)$_q$—S(O)$_r$R$^f$; —(CH$_2$)$_q$—NR$^g$R$^h$; —(CH$_2$)$_q$—C(=O)—NR$^g$R$^h$; —(CH$_2$)$_q$—C(=O)—C(=O)—NR$^g$R$^h$; —(CH$_2$)$_q$—SO$_2$—NR$^g$R$^h$; —(CH$_2$)$_q$—N(R$^f$)—C(=O)—R$^i$; —(CH$_2$)$_q$—C(=O)—R$^i$; or —(CH$_2$)$_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Polar aprotic solvent" means a solvent comprised of molecules having polar groups thereon, but without mobile protons. Exemplary polar aprotic solvents include, without limitation, dimethyl formamide, acetonitrile, dimethyl sulfoxide, N,N-dimethyl acetamide, N-methylpyrrolidinone, tetrahydrofuran, dioxane, ethyl acetate, tetrahydropyran, pyridine, acetone, 2-propanone, 2-butanone, ethylene glycol dimethyl ether, methylene chloride, chloroform, and the like.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solution" as used herein is meant to encompass liquids wherein a reagent or reactant is present in a solvent in dissolved form (as a solute) or is present in particulate, undissolved form, or both. Thus, in a "solution", it is contemplated that the solute may not be entirely dissolved therein and solid solute may be present in dispersion or slurry form. Accordingly, a "solution" of a particular reagent or reactant is meant to encompasses slurries and dispersions, as well as solutions, of such reagents or reactants. "Solution" and "Slurry" may be used interchangeable herein.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disease states" associated with serotonin and norepinephrine neurotransmission include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, haemorrhage, and disorders and disease states of the urinary tract.

"Depression" as used herein includes, but is not limited to, major depression, long-term depression, dysthymia, mental states of depressed mood characterised by feelings of sadness, despair, discouragement, "blues", melancholy, feelings of low self esteem, guilt and self reproach, withdrawal from interpersonal contact, and somatic symptoms such as eating and sleep disturbances.

"Anxiety" as used herein includes, but is not limited to, unpleasant or undesirable emotional states associated with psychophysiological responses to anticipation of unreal, imagined or exaggerated danger or harm, and physical concomitants such as increased heart rate, altered respiration rate, sweating, trembling, weakness and fatigue, feelings of impending danger, powerlessness, apprehension and tension.

"Disorders of the urinary tract" or "uropathy" used interchangeably with "symptoms of the urinary tract" means the pathologic changes in the urinary tract. Examples of urinary tract disorders include, but are not limited to, stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvodynia, urethritis, orchidalgia, overactive bladder, and the like.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28th Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. For convenience, the IUPAC numbering of the positions of representative indole and related compounds described herein is shown by the formula:

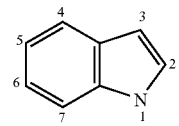

Whenever a chiral carbon is present in a chemical structure, it is intended that all stereoisomers associated with that chiral carbon are encompassed by the structure.

All patents and publications identified herein are incorporated herein by reference in their entirety.

METHODS OF THE INVENTION

The methods of the invention will be more fully understood by making reference to Scheme A below, wherein:

m is from 0 to 4;

Ar is optionally substituted aryl or optionally substituted heteroaryl;

each R is any $C_{1-4}$alkyl; and each $R^1$ is independently: alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —$(CH_2)_q$—S(O)$R^f$; —$(CH_2)_q$—NR$^g$R$^h$; —$(CH_2)_q$—C(=O)—NR$^g$R$^h$; —$(CH_2)_q$—C(=O)—C(=O)NR$^g$R$^h$; —$(CH_2)_q$—SO$_2$—NR$^g$R$^h$; —$(CH_2)_q$—N(R$^f$)—C(=O)R$^i$; —$(CH_2)_q$—C(=O)—R$^i$; or —$(CH_2)_q$—N(R$^f$)—SO$_2$—R$^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy.

SCHEME A

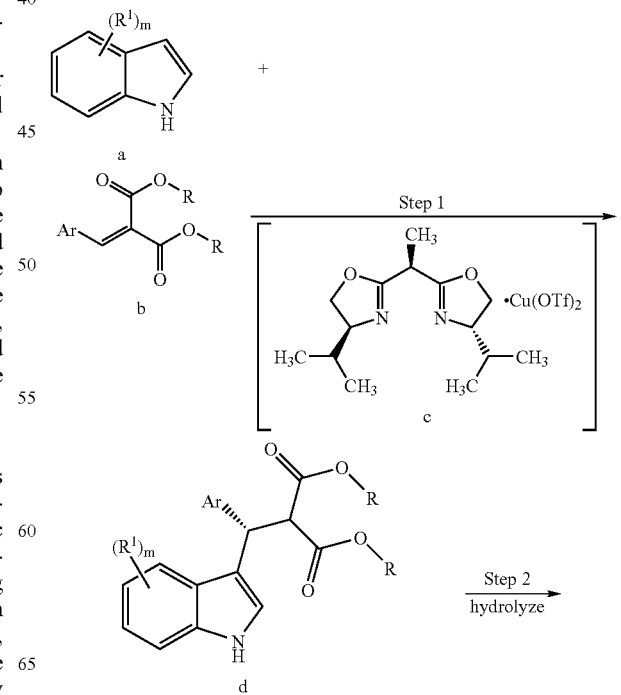

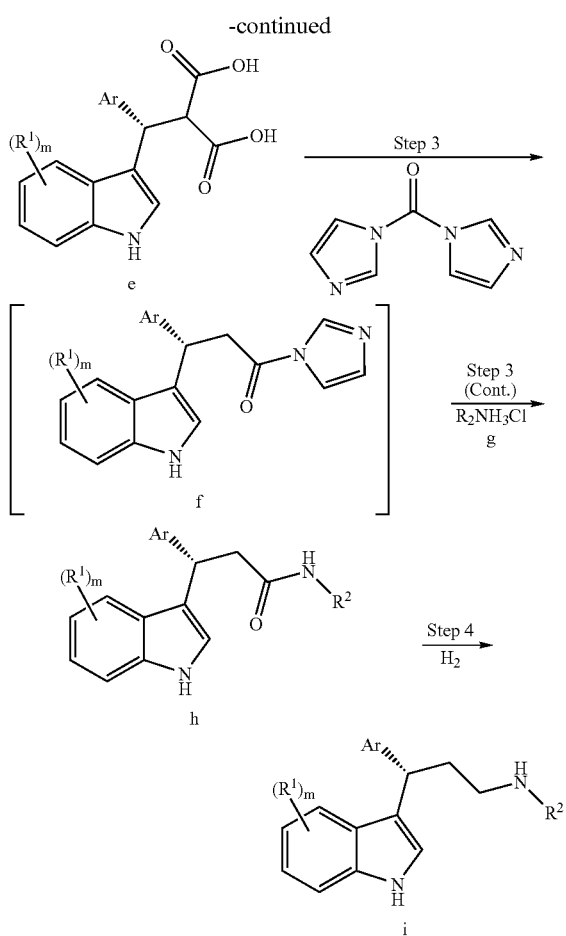

h to a methylene, and thus afford aminopropyl indole i. The reaction of step 4 may be carried out under polar aprotic solvent conditions such as in tetrahydrofuran. In many embodiments a hydrogen-releasing reagent such as vitride (sodium dihydro-bis-2-methoxyethoxy)aluminate) may be used for the hydrogenation in step 4. In other embodiments a reducing agent such as lithium aluminum hydride may be used. In still other embodiments the hydrogenation of step 4 may be achieved by used of a platinum or palladium catalyst in the presence of hydrogen gas.

Accordingly, in certain embodiments the method of the invention comprises:

hydrogenating an indole propionamide compound of formula h

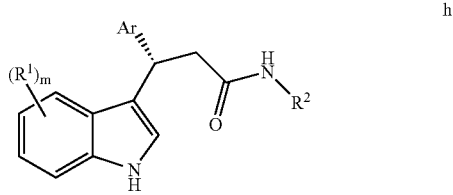

wherein:
m is from 0 to 4;
Ar is optionally substituted aryl or optionally substituted heteroaryl;
each $R^1$ is independently alkoxy, cyano, alkyl, halo, —S(O)$_r$R$^a$; or —C(=O)NR$^b$R$^c$ wherein r is an integer from 0 to 2, and each of R$^a$, R$^b$, and R$^c$ is independently hydrogen or alkyl; and
$R^2$ is alkyl;

with vitride, to form an aminopropyl indole compound of formula i

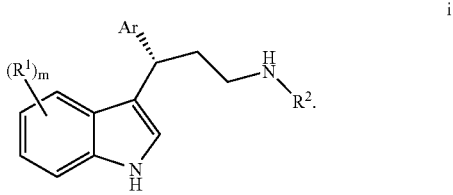

In certain embodiments, m is 0, 1 or 2 and each $R^1$ is independently alkoxy, halo or cyano.

In certain embodiments, m is 1 and $R^1$ is alkoxy, halo or cyano.

In certain embodiments, m is 1 and $R^1$ is methoxy.

In certain embodiments, Ar is optionally substituted phenyl.

In certain embodiments, $R^2$ is methyl.

In certain embodiments, m is 1 and $R^1$ is located at the 4-position of the indole ring system.

In certain embodiments, m is 1 and $R^1$ is alkoxy, halo or cyano located at the 4-position of the indole ring system.

In certain embodiments, m is 1, $R^1$ is methoxy located at the 4-position of the indole ring system, and $R^2$ is methyl.

In certain embodiments, the hydrogenation of indole propionamide h may be carried out under polar aprotic solvent conditions. Preferably, the hydrogenation of indole propionamide h is carried out in tetrahydrofuran.

In step 1 of the procedure of Scheme A, an optionally substituted indole a is reacted with aryl malonate b in the presence of the chiral catalyst c generated from 1,1'-bis[2-(4-(S)-isopropyl-1,3-oxazolinyl)]ethane and copper(II) trifluoromethanesulfonate to form an indole malonate compound d. This reaction may be carried out under polar protic solvent conditions, such as in the presence of an alcohol such as sec-butanol. The indole malonate compound d is shown as an (S) stereoisomer. It should be readily understood that the chirality of the copper triflate catalyst may be varied to provide the (R) isomer if desired.

The indole malonate d is hydrolyzed in step 2 to provide indole malonic acid compound e. The reaction of step 2 may be carried out by treatment of malonate d with base, such as KOH, NaOH or the like, under polar protic solvent conditions. One preferred solvent system for step 2 is a mixture of tetrahydrofuran and water, with KOH used as base.

In step 3, indole malonic acid compound e is treated with di-imidazol-1-yl-methanone (carbonyl diimidazole), to form an imidazolone compound f. In many embodiments the imidazolone compound f need not be isolated, and alkylamine g may be added directly to the reaction mixture, following the di-imidazol-1-yl-methanone, to afford indole propionamide compound h. The reaction(s) of step 3 may be carried out under polar aprotic solvent conditions, such as dichloromethane. In certain embodiments a trialkylamine catalyst such as diisopropylethyl amine may be present.

In step 4, indole propionamide h is subject to hydrogenation/reduction to reduce the carbonyl group of propionamide In certain embodiments, the hydrogenation of indole propionamide h may be carried out using vitride as a hydrogenating/reducing agent.

In many embodiments, the method of the invention may further comprise:

treating an indole malonic acid compound of formula e

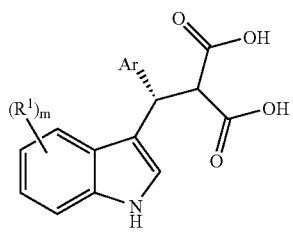

wherein m, $R^1$ and Ar are as defined herein, with di-imidazol-1-yl-methanone, followed by an alkylamine $R^2NH_2$ g to form the indole propionamide of formula h.

In certain embodiments, the treating of indole malonic acid e with di-imidazol-1-yl-methanone, followed by an alkylamine $R^2NH_2$ g, may be carried out under polar aprotic solvent conditions. In one preferred embodiment the treating of indole malonic acid e with di-imidazol-1-yl-methanone, followed by an alkylamine $R^2NH_2$ g is carried out in dichloromethane.

In certain embodiments, the treating of indole malonic acid e with di-imidazol-1-yl-methanone, followed by an alkylamine $R^2NH_2$ g may be carried out in the presence of a trialkylamine catalyst such as diisopropylethyl amine.

In certain embodiments the method of the invention further comprises:

hydrolyzing an indole malonate compound of formula d

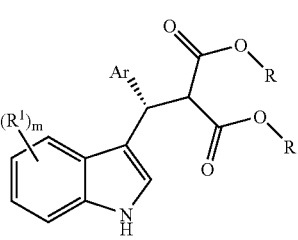

wherein:
each R is alkyl and may be the same or different; and
m, $R^1$ and Ar are as defined herein, to form the indole malonic acid compound e.

In certain embodiments the hydrolyzing of indole malonate compound d may be carried out under basic conditions.

In certain embodiments the hydrolyzing of indole malonate compound d may be carried out in the presence of KOH.

In certain embodiments the hydrolyzing of indole malonate compound d may be carried out under polar protic solvent conditions.

In certain embodiments the hydrolyzing of indole malonate compound d may be carried out in the presence of ethylene diamine tetraacetate salt.

In certain embodiments the hydrolyzing of indole malonate compound d may be carried out in a mixture of tetrahydrofuran and water.

In certain embodiments the method of the invention may further comprise:

reacting an indole compound of formula a

wherein m and $R^1$ are as defined herein, with an aryl malonate of formula b

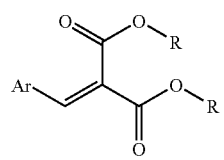

wherein Ar and R are as defined herein, in the presence of a copper triflate catalyst of formula c

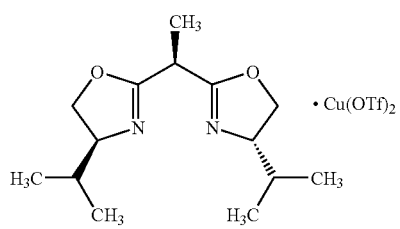

to form the indole malonate compound of formula d

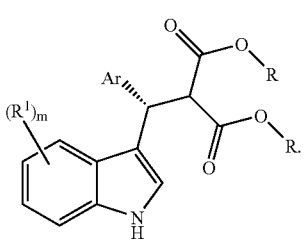

In certain embodiments the reacting of indole compound of formula a with aryl malonate of formula b in the presence of catalyst c may be carried out under polar protic solvent conditions.

In certain embodiments the reacting of indole compound of formula a with aryl malonate of formula b in the presence of catalyst c may be carried out in an alcohol solvent. One preferred solvent is 2-butanol.

COMPOUNDS OF THE INVENTION

The invention provides compounds of formula h:

h wherein:
m is from 0 to 4;
Ar is optionally substituted aryl or optionally substituted heteroaryl;
each $R^1$ is independently alkoxy, cyano, alkyl, halo, —S(O)$_r R^a$; or —C(=O)NR$^b R^c$ wherein r is an integer from 0 to 2, and each of $R^a$, $R^b$, and $R^c$ is independently hydrogen or alkyl; and
$R^2$ is alkyl;
provided that when $R^2$ is methyl, then m is not 0, or provided that when $R^2$ is methyl, then Ar is not pyridin-4-yl.

Compounds of formula h are useful as intermediates in the methods of the invention.

In certain embodiment of formula h, m is 0, 1 or 2 and each $R^1$ is independently alkoxy, halo or cyano.

In certain embodiments of formula h, m is 1 and $R^1$ is alkoxy, halo or cyano.

In certain embodiments of formula h, m is 1 and $R^1$ is methoxy.

In certain embodiments of formula h, Ar is optionally substituted phenyl.

In certain embodiments, $R^2$ is methyl.

In certain embodiments of formula h, m is 1 and $R^1$ is located at the 4-position of the indole ring system.

In certain embodiments of formula h, m is 1 and $R^1$ is alkoxy, halo or cyano located at the 4-position of the indole ring system.

In certain embodiments of formula h, m is 1, $R^1$ is methoxy located at the 4-position of the indole ring system, and $R^2$ is methyl.

The invention also provides compounds of formula d:

wherein:
m is from 0 to 4;
Ar is optionally substituted aryl or optionally substituted heteroaryl;
each R is alkyl and may be the same or different;
each $R^1$ is independently alkoxy, cyano, alkyl, halo, —S(O)$_r R^a$; or —C(=O)NR$^b R^c$ wherein r is an integer from 0 to 2, and each of $R^a$, $R^b$, and $R^c$ is independently hydrogen or alkyl; and
each R is alkyl and may be the same or different.

Compounds of formula d are useful as intermediates in the methods of the invention.

In certain embodiment of formula d, m is 0, 1 or 2 and each $R^1$ is independently alkoxy, halo or cyano.

In certain embodiments of formula d, m is 1 and $R^1$ is alkoxy, halo or cyano.

In certain embodiments of formula d, m is 1 and $R^1$ is methoxy.

In certain embodiments of formula d, Ar is optionally substituted phenyl.

In certain embodiments, $R^2$ is methyl.

In certain embodiments of formula d, m is 1 and $R^1$ is located at the 4-position of the indole ring system.

In certain embodiments of formula d, m is 1 and $R^1$ is alkoxy, halo or cyano located at the 4-position of the indole ring system.

In certain embodiments of formula d, m is 1, $R^1$ is methoxy located at the 4-position of the indole ring system, and $R^2$ is methyl.

In certain embodiments of formula d, each R is independently methyl or ethyl. Preferably R is ethyl.

Where any of $R^1$, $R^2$, $R^3$, $R^4$, $R^5$, $R^6$, $R^7$, $R^a$, $R^b$, $R^c$, $R^d$, $R^e$, $R^f$, $R^g$ or $R^h$ herein are alkyl or contain an alkyl moiety, such alkyl is preferably lower alkyl, i.e. $C_1$-$C_6$alkyl, and more preferably $C_1$-$C_4$alkyl.

Utility

The subject methods provides compounds that are usable for the treatment of diseases or conditions associated with serotonin neurotransmission and/or norepinephrine neuortransmission. Such diseases and conditions include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, and haemorrhage.

The methods of the invention also provide compounds usable for treatment of disorders and disease states of the urinary tract such as stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity.

The methods of the invention also provide compounds having anti-inflammatory and/or analgesic properties in vivo, and accordingly, which are expected to find utility in the treatment of disease states associated with pain conditions from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Additional useful compounds that may be prepared using the methods of the invention are disclosed in U.S. patent application Ser. No. 11/142,076 filed on Dec. 1, 2005, which is incorporated herein by reference.

ADMINISTRATION AND PHARMACEUTICAL COMPOSITION

The compounds prepared by the methods of the invention may be used in pharmaceutical compositions comprising at least one such compound or a pharmaceutically acceptable salt or solvate thereof, together with at least one pharmaceutically acceptable carrier, and optionally other therapeutic and/or prophylactic ingredients.

In general, the compounds prepared according to the methods of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds made by the methods of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds made by the methods of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds made by the methods of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds made by the methods of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds made by the methods of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds made by the methods of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds made by the methods of the invention may be formulated for vaginal administration. Pessaries, tampons, creams, gels, pastes, foams or sprays containing in addition to the active ingredient such carriers as are known in the art to be appropriate.

The compounds made by the methods of the invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds made by the methods of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

Abbreviations

DCM dichloromethane/methylene chloride
DMF N,N-dimethylformamide
DMAP 4-dimethylaminopyridine
EtOAc ethyl acetate
EtOH ethanol
gc gas chromatography
HMPA hexamethylphosphoramide
hplc high performance liquid chromatography
mCPBA m-chloroperbenzoic acid
MeCN acetonitrile
NMP N-methylpyrrolidinone
TEA triethylamine
THF tetrahydrofuran
LDA lithium diisopropylamine
TLC thin layer chromatography

Preparation 1

Bis-(4-Isopropyl-4,5-dihydro-oxazolo)-methane Cu(OTf)₂ Catalyst Complex Preparation Copper (II) triflate (614.9 g) and 2-butanol (35 L) were added to a 100 L reactor. The mixture was stirred for 20 minutes at 35 degrees C. The mixture was then cooled to 24 degrees C. and stirred for 20 minutes. A solution of the ligand i-PrBOX (generated from 1,1'-bis[2-(4-(S)-isopropyl-1,3-oxazolinyl)]ethane and copper(II) trifluoromethanesulfonate, 686.4 g, as described in Chem. Comm. 2004, p. 432) in 2-butanol (2 L) was added, followed by 3 L of 2-butanol that was used to rinse the flask containing the ligand solution. The catalyst complex was stirred for 30 minutes at 24 degrees C. before use in the example below.

Example 1

The synthetic procedure of this example is outlined in Scheme B.

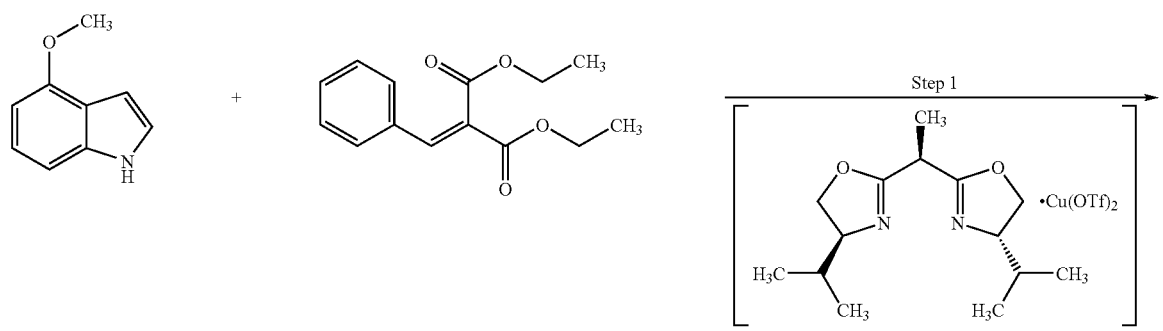

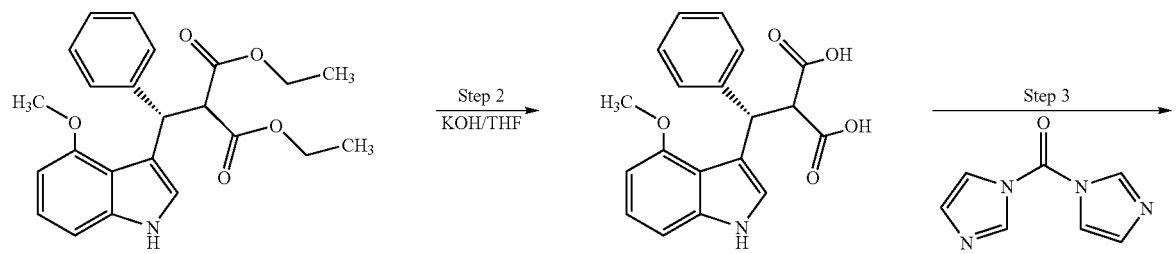

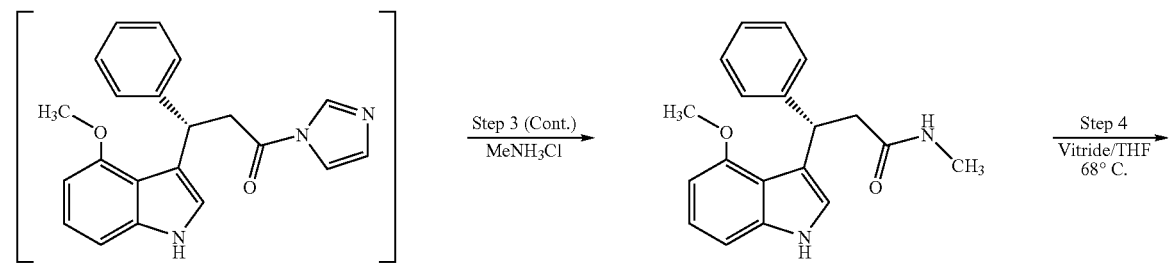

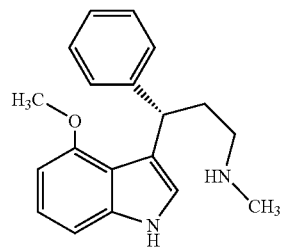

Step 1 2-[(S)-(4-Methoxy-1H-indol-3-yl)-phenyl-methyl]-malonic acid diethyl ester

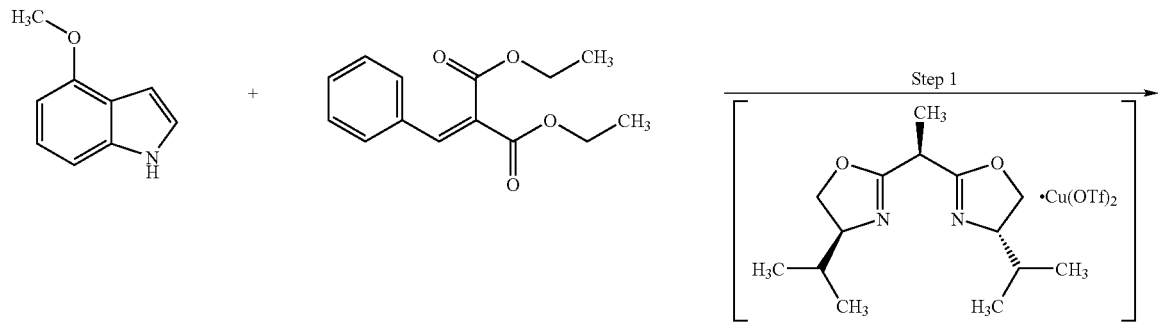

A 200 L reactor under N₂ atmosphere was charged with 4-methoxyindole (5 kg) and 2-butanol (20 L). The preformed catalyst complex 1,1'-bis[2-(4-(S)-isopropyl-1,3-oxazolinyl)]ethane Cu(OTf)₂ from preparation 1 above was added to the reactor, and the catalyst transfer line was rinsed with 2-butanol (5 L), which was also added to the reactor. The reactor was cooled to −15 degrees C., and diethylbenzylldene malonate (9.28 kg) was added over a 30 minute period, and the transfer line was rinsed with 2-butanol, which was added to the reactor. The reaction was stirred overnight at −10 degrees C. A 10 mL aliquot was taken and subject to HPLC, which showed less than 1.5% of the starting 4-methoxyindole was present, indicating that the reaction was complete. The reactor contents were then warmed to 0 degrees C. and water (60 L) was added. The reaction mixture was stirred for one hour and allowed to warm to 5 degrees C., during which time crystalline 2-[(S)-(4-methoxy-1H-indol-3-yl)-phenyl-methyl]-malonic acid diethyl ester formed by precipitation. The crystals were then collected by filtration on a Rosenmund filter and washed with a 1:1 mixture of ethanol and water. The off-white crystals were then dried at about 70 degrees C. for 24 hours, affording 12.085 kg of 2-[(S)-(4-methoxy-1H-indol-3-yl)-phenyl-methyl]-malonic acid diethyl ester (90.0% yield). ¹H nmr (CDCl₃ at 57 degrees C.) delta: 0.950 (t, 3H, J=7.11 Hz), 0.987 (t, 3H, J=7.11 Hz), 3.81 (s, 3H), 3.96 (m, 4H), 4.29(d, 1H, J=11.9 Hz), 5.50 (d, 1H, J=11.9 Hz), 6.39(d, 1H, J=7.72 Hz), 6.84 (d, 1H, J=8.10 Hz), 6.96-7.09 (m, 3H), 7.16 (m, 2H), 7.34 (m, 2H), 8.01 (bs, 1H). Mp=134-136° C.

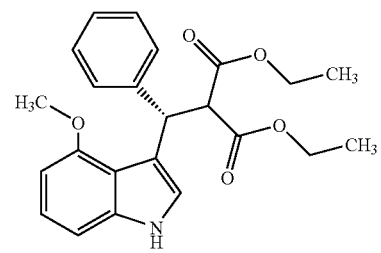

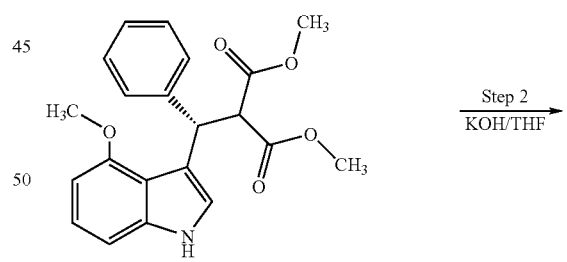

Step 2 2-[(S)-(4-Methoxy-1H-indol-3-yl)-phenyl-methyl]-malonic acid

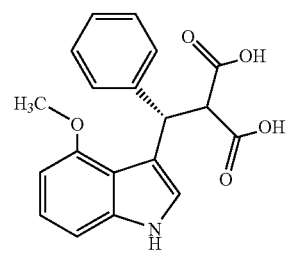

A 200 L reactor under $N_2$ atmosphere was loaded with 2-[(S)-(4-methoxy-1H-indol-3-yl)-phenyl-methyl]-malonic acid diethyl ester (12 kg) and THF (53 kg). A solution of EDTA tetrasodium decahydrate (8 kg) in 20 L of cold tap water was separately prepared with shaking to dissolve the solid. One half of the EDTA tetrasodium decahydrate solution was added to the reactor, and the mixture was agitated for 10 minutes. The layers were allowed to separate over 20 minutes, and the aqueous phase was drained. The remaining EDTA tetrasodium decahydrate solution was added to the reactor and the mixture was agitated for 10 minutes before allowing the phases to separate over 20 minutes. The aqueous phase was drained, and saturated aqueous NaCl solution (14.4 kg) was added to the reactor. The mixture was agitated for five minutes, after which the phases were allowed to separate over 20 minutes. The aqueous phase was drained from the reactor, and cold tap water (55 L) was added to the reactor and agitation. KOH (50 wt %, 27.2 kg) was added, and the reactor was configured for reflux. The mixture was heated at 60-65 degrees C. (jacket temperature) overnight. A 10 mL aliquot of the reaction mixture was taken, and HPLC showed the amount of starting material and monoester were <2%. The reaction mixture was then cooled to 22 degrees C. and toluene (52 kg) was added, the contents were agitated for five minutes and then the layers were allowed to separate. The aqueous product layer was separated, combined with isopropanol (37.9 kg), and then acidified with concentrated HCl (41.4 kg). Cooling and stirring were applied during addition to maintain the internal reactor temperature below 30 degrees C. The product slowly precipitated out of solution. Once a thick slurry was formed, cold tap water (72 L) was added, the reactor jacket temperature was set at 5 degrees C., and the slurry was aged one hour. The mixture was filtered on a Rosenmund filter and collected solid was washed twice with cold tap water (50 L). The product was dried in a vacuum oven at 70 degrees C. with $N_2$ bleed to afford 2-[(S)-(4-Methoxy-1H-indol-3-yl)-phenyl-methyl]-malonic acid as an off-white crystalline solid (8.772 kg, 86% yield). $^1$H mm (CDCl$_3$): 3.80 (s, 3H), 4.28 (d, 2H, J=12.4 Hz), 5.43 (d, 2H, J=12.4 Hz), 6.35 (dd, 1H, J=1.08 Hz, J=7.41), 6.86-6.96 (m, 2H), 7.07 (m, 1H), 7.17 (m, 3H), 7.37 (m, 2H). Mp=155-157° C.

Step 3 (S)-3-(4-Methoxy-1H-indol-3-yl)-N-methyl-3-phenyl-propionamide

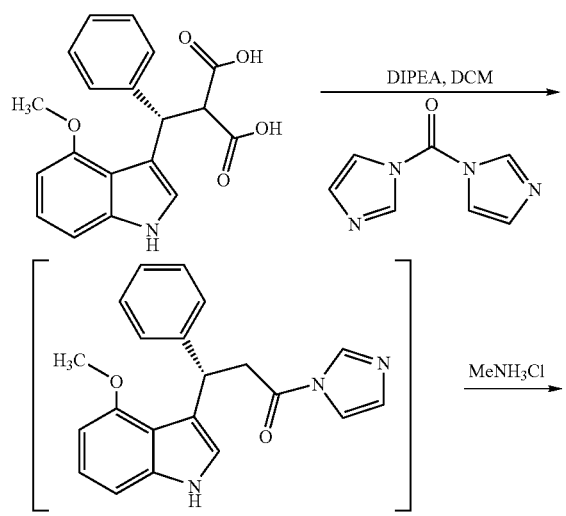

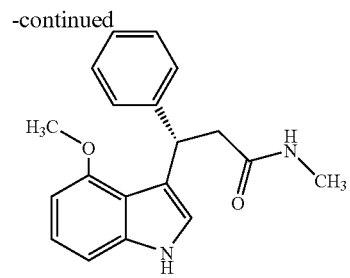

A 200 L reactor under $N_2$ atmosphere was charged with 2-[(S)-(4-Methoxy-1H-indol-3-yl)-phenyl-methyl]-malonic acid (8.0 kg) and methylene chloride (53 kg).

Diisopropylethyl amine (3.35 kg) was added slowly so that the internal reactor temperature did not exceed 30 degrees C., and the addition line was rinsed forward to the reactor with methylene chloride (1 kg). The mixture was stirred for 15 minutes, and then carbonyl diimidazole (4.01 kg) was added. $CO_2$ was released during the addition, and the rate of addition was controlled to limit the foaming during the off gassing of $CO_2$. The mixture was stirred at 22 degrees C. for one hour. A 10 mL aliquot of the reactor contents was subject to HPLC, which showed that more than 95% of the 2-[(S)-(4-methoxy-1H-indol-3-yl)-phenyl-methyl]-malonic acid starting material had been converted to (S)-1-Imidazol-1-yl-3-(4-methoxy-1H-indol-3-yl)-3-phenyl-propan-1-one (not isolated).

Methylamine hydrochloride (2.04 kg) was added, and the reactor contents were stirred at 22 degrees C. overnight. A 10 mL aliquot of the reactor contents was taken, from which HPLC indicated completion (<1% of (S)-1-Imidazol-1-yl-3-(4-methoxy-1H-indol-3-yl)-3-phenyl-propan-1-one) of the reaction. Cold tap water (64 L) was added, followed by isopropyl alcohol (8.2 kg). The reactor was set up for atmospheric distillation, and the reactor jacket was heated at 85 degrees C. and methylene chloride was removed by distillation until the reactor temperature reached 70 degrees C. The reactor was gradually cooled to 22 degrees C. and the resulting slurry was stirred for one hour. The product was filtered on a Nutsche filter, and the collected solid was washed with water-isopropyl alcohol (1:1) and dried at 70 degrees C. to afford (S)-3-(4-methoxy-1H-indol-3-yl)-N-methyl-3-phenyl-propionamide as an off-white crystalline solid, (7.094 kg, 98% yield). $^1$H nmr (DMSO-d6): 2.48 (d, 3H, J=4.56 Hz), 2.60-2.90 (m, 2H), 3.69 (s, 3H), 5.05 (t, 1H, J=7.95 Hz), 6.34 (m, 1H), 6.90 (m, 2H), 7.08 (m, 2H), 7.20 (m, 4H), 7.75 (bq, 1H, J=4.56 Hz), 10.8 (bs, 1H). Mp=178-181° C.

Step 4 [(S)-3-(4-Methoxy-1H-indol-3-yl)-3-phenyl-propyl]-methyl-amine

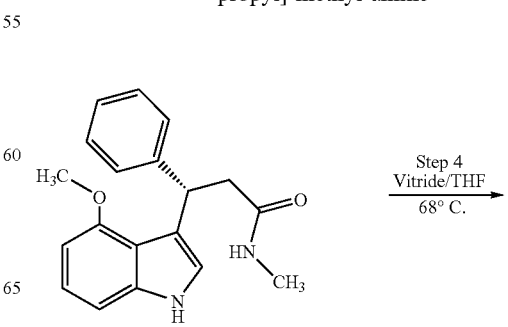

-continued

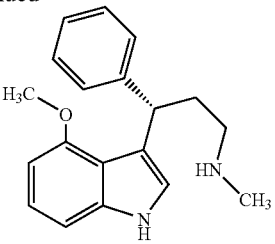

A 200 L reactor under N₂ atmosphere was charged with (S)-3-(4-methoxy-1H-indol-3-yl)-N-methyl-3-phenyl-propionamide (7.09 kg) and THF (63 kg), and the mixture was stirred while cooling to 5 degrees C. Vitride (sodium dihydrobis-2-methoxyethoxy)aluminate, 17.85 kg) was added over 1.5 hours, during which time H₂ evolved. The addition was controlled to avoid excessive foaming and to allow the internal reactor temperature to remain below 15 degrees C. After completion of the vitride addition, the reactor temperature was raised to 50 degrees C. After 1 hour at 50 degrees, the reactor was heated to reflux (68 degrees C.) for 2 hours. A 10 mL aliquot of the reactor contents was taken and subject to HPLC, which showed <3% of the propionamide starting material remained. The reaction was allowed to cool to ambient temperature overnight under N₂ atmosphere.

A second 200 L reactor was loaded with Rochelle salt (58.3 kg) and tap water (58.3 L). The mixture was stirred at 30-40 degrees C. until all the solids went into solution. The mixture was then cooled at 15 degrees C. The contents of the first reactor were slowly added to the Rochelle salt solution under flowing N₂ atmosphere, during which time hydrogen gas evolved. The quenched reaction mixture was allowed to separate and the aqueous layer was removed. The aqueous layer was back extracted with ethyl acetate (64 kg), and the aqueous layer was drained. The ethyl acetate and THF layers were combined and washed twice with tap water (28.4 kg). The phases were separated and the solvent was distilled from the organic layer at atmospheric pressure until the reactor temperature reached 78 degrees C. Ethyl acetate (53 L) was added to obtain a 7.5 to 1 mixture of ethyl acetate to product. The distillation was continued until the reactor temperature again reached 78 degrees C. The reactor was then cooled to 10 degrees C. over 10 hours, and heptane was added. The reactor was maintained at 10 degrees C. for 2 hours, and then the resulting precipitate was collected by filtration on a Rosemund filter. The collected solid was washed with ethyl acetate/heptane (6.4 kg/9.7 kg) and dried at 70 degrees C. under house vacuum and a stream of nitrogen, affording 4.8030 kg of 4 [(S)-3-(4-methoxy-1H-indol-3-yl)-3-phenyl-propyl]-methyl-amine as an off-white crystalline solid (72.3% yield). ¹H mm (DMSO-d6): 1.97-2.08 (m, 1H), 2.21 (m, 4H), 2.31-2.44 (m, 2H), 3.74 (s, 3H), 4.58 (t, 1H, J=8.07), 6.35 (m, 1H), 6.90 (m, 2H), 7.05 (m, 2H), 7.18-7.28 (m, 4H), 10.9 (bs, 1H). Mp=134-137° C. $\alpha_D^{25\,C}$=62° (c=10 mg/mL).

Example 2

Screening for Human Serotonin Transporter (hSERT) Antagonists Using a Scintillation Proximity Assay (SPA)

The screening assay of this example was used to determine the affinity of ligands at the hSERT transporter by competition with [³H]-Citalopram.

Scintillation Proximity Assay (SPA) works by bringing radioligand within close proximity to the bead's scintillant to stimulate light emission. In this assay, the receptor-containing membranes were pre-coupled to the SPA beads and the binding of the appropriate radioligand to the transporter was measured. The light emission was proportional to the amount of bound radioligand. Unbound radioligand produced no signal as a result of distant proximity to scintillant (lack of energy transfer).

HEK-293 cells (Tatsumi et al., Eur. J. Pharmacol. 1997, 30, 249-258) stably expressing recombinant hSERT were maintained with media (DMEM high glucose with 10% FBS, 300 µg/ml G418 and 2 mM L-Glutamine) and incubated at 37° C. with 5% CO₂. Cells are released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10⁹ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3 mg/ml (w:v). and stored at −80° C.

For Scintillation Proximity Assay IC₅₀/K_i determination, 50 mM Tris-HCl and 300 mM NaCl, (pH 7.4) buffers were utilized. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the [³H]-Citalopram radioligand was added at 50 µl/well. Membrane and beads were prepared to a ratio of 10 µg: 0.7 mg, with 0.7 mg PVT-WGA Amersham beads (Cat#RPQ0282V) added per well. 130 µl of the membrane: bead mixture was added to the assay plate. The mixtures were allowed to stand at room temperature for one hour, and were then counted on a Packard TopCount LCS, a generic Scintillation Proximity Assay counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound counts per minute (CPM) at maximum concentration-Non-Specific CPM)/Total CPM*100]. The concentration producing 50% inhibition (IC₅₀) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds prepared by the methods of the invention were found to have affinity for human serotonin transporter. For example, [3-(4-Methoxy-1H-indol-3-yl)-3-phenyl-propyl]-methyl-amine exhibited an $IC_{50}$ of approximately 8.90 using the above assay.

Example 3

Screening for Compounds Active at Human Norepinephrine Transporter (hNET) Using a Scintillation Proximity Assay (SPA)

This assay was used to determine the affinity of ligands for the hNET transporter by competition with [$^3$H]-Nisoxetine. As in the hSERT assay of the above example, receptor-containing membranes were pre-coupled to the SPA beads and the binding of the appropriate radioligand to the transporter was measured. The light emission was proportional to the amount of bound radioligand, with unbound radioligand producing no signal.

HEK-293 cells (Tatsumi et al., Eur. J. Pharmacol. 1997, 30, 249-258) stably expressing recombinant hNET (Clone: HEK-hNET #2) were maintained with media (DMEM hi glucose with 10% FBS, 300 μg/ml G418 and 2 mM L-Glutamine) and incubated at 37° C. with 5% $CO_2$. Cells were released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3-6 mg/ml (w:v). and stored at −80° C.

$^3$[H] Nisoxetine radioligand (Amersham Cat. #TRK942 or Perkin Elmer Cat. #NET1084, specific activity: 70-87 Ci/mmol, stock concentration: 1.22e-5 M, final concentration: 8.25e-9 M), and 50 mM Tris-HCl, 300 mM NaCl, (pH 7.4) buffers were used for Scintillation Proximity Assay $IC_{50}/K_i$ determination. Compounds of the invention were diluted from 10 mM to 0.1 nM FAC (10 point curves, whole log/half log dilutions) via a Beckman Biomek 2000 using a serial dilution protocol. The test compounds were then transferred (20 μl/well) and the radioligand was added at 50 μl/well. Membrane and beads were prepared to a ratio of 10 μg: 0.7 mg, with 0.7 mg PVT-WGA Amersham beads (Cat#RPQ0282V) added per well. 130 μl of the membrane: bead mixture was added to the assay plate. The mixtures were allowed to stand at room temperature for one hour, and were then counted on a Packard TopCount LCS, a generic SPA counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds prepared by the methods of the invention were found to have affinity for the human norepinephrine transporter. For example, [3-(4-Methoxy-1H-indol-3-yl)-3-phenyl-propyl]-methyl-amine exhibited an $IC_{50}$ of approximately 8.19 using the above assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for preparing a compound of formula i:

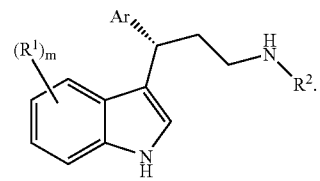

wherein:
  m is from 0 to 4;
  Ar is optionally substituted aryl or optionally substituted heteroaryl;
  each $R^1$ is independently alkoxy, cyano, alkyl, halo, —S(O)$_r$R$^a$; or —C(=O)NR$^b$R$^c$ wherein r is an integer from 0 to 2, and each of R$^a$, R$^b$, and R$^c$ is independently hydrogen or alkyl; and
  $R^2$ is alkyl;
the method comprising hydrogenating an indole propionamide compound of formula h

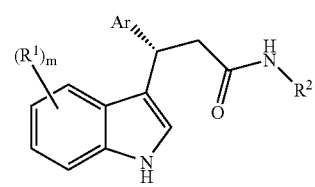

with vitride, to form the aminopropyl indole compound of formula i.

2. The method of claim 1, wherein m is 0, 1 or 2 and each $R^1$ is independently alkoxy, halo or cyano.

3. The method of claim 1, wherein m is 1 and $R^1$ is alkoxy, halo or cyano.

4. The method of claim 1, wherein m is 1 and $R^1$ is methoxy.

5. The method of claim 1, wherein Ar is optionally substituted phenyl.

6. The method of claim 1, wherein $R^2$ is methyl.

7. The method of claim 1, wherein m is 1 and $R^1$ is located at the 4-position of the indole ring system.

8. The method of claim 5, wherein m is 1 and $R^1$ is alkoxy, halo or cyano located at the 4-position of the indole ring system.

9. The method of claim 5, wherein m is 1, $R^1$ is methoxy located at the 4-position of the indole ring system, and $R^2$ is methyl.

10. The method of claim 1, wherein the hydrogenation of indole propionamide h is carried out under polar aprotic solvent conditions.

11. The method of claim 10, wherein the hydrogenation of indole propionamide h is carried out in tetrahydrofuran.

12. The method of claim 10, wherein the hydrogenation of indole propionamide h is carried out using vitride as a hydrogenating agent.

13. The method of claim 1, further comprising:
treating an indole malonic acid compound of formula e

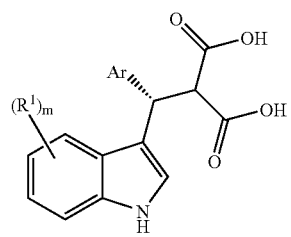

e wherein m, $R^1$ and Ar are as defined herein,
with di-imidazol-1-yl-methanone, followed by an alkylamine $R^2NH_2$ g to form the indole propionamide of formula h.

14. The method of claim 13, further comprising:
hydrolyzing an indole malonate compound of formula d

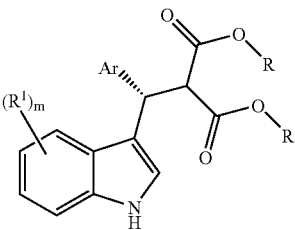

d wherein:
each R is alkyl and may be the same or different; and
m, $R^1$ and Ar are as defined herein,
to form the indole malonic acid compound e.

15. The method of claim 14, further comprising:
reacting an indole compound of formula a

a wherein m and $R^1$ are as defined herein,
with an aryl malonate of formula b

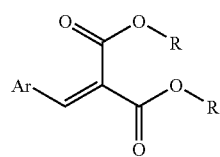

b wherein Ar and R are as defined herein,
in the presence of a copper triflate catalyst of formula c

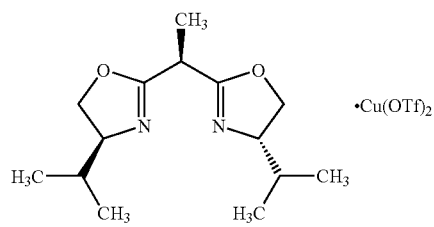

c to form the indole malonate compound of formula d

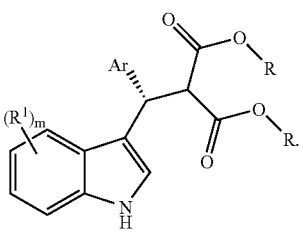

d

* * * * *